United States Patent [19]

Cavazza et al.

[11] Patent Number: 4,859,698

[45] Date of Patent: Aug. 22, 1989

[54] NOVEL CLASS OF ACYL-DERIVATIVES OF CARNITINE, PROCESS FOR PREPARING SAME AND THERAPEUTIC USE THEREOF

[75] Inventors: Claudio Cavazza; Paolo De Witt; Maria O. Tinti, all of Rome, Italy

[73] Assignee: Sigma-Tau Industrie Farmaceutiche Riunite S.p.A., Rome, Italy

[21] Appl. No.: 200,641

[22] Filed: May 31, 1988

Related U.S. Application Data

[60] Division of Ser. No. 68,748, Jun. 30, 1987, Pat. No. 4,766,222, which is a continuation of Ser. No. 753,653, Jul. 10, 1985, abandoned, which is a continuation of Ser. No. 433,427, Oct. 8, 1982, abandoned, which is a continuation of Ser. No. 237,312, Feb. 23, 1981, abandoned.

[30] Foreign Application Priority Data

Mar. 6, 1980 [IT] Italy .................................. 48099 A/80

[51] Int. Cl.$^4$ ................... C07D 333/22; C07D 333/32
[52] U.S. Cl. ..................................... 514/445; 514/446; 514/448; 549/64; 549/65; 549/71; 549/72
[58] Field of Search ....................... 549/64, 65, 71, 72; 514/446, 445, 448

[56] References Cited

U.S. PATENT DOCUMENTS

| | | | |
|---|---|---|---|
| 4,599,350 | 7/1986 | Gayer et al. | 549/64 |
| 4,668,800 | 5/1987 | Meyer et al. | 549/64 |
| 4,707,491 | 11/1987 | Covey et al. | 514/445 |

*Primary Examiner*—Richard L. Raymond
*Assistant Examiner*—Raymond Covington
*Attorney, Agent, or Firm*—Ladas & Parry

[57] ABSTRACT

A novel class of acyl-derivatives of carnitine is disclosed wherein the acyl radical is either the radical of unsaturated organic acids (typically, acrylic acid) or the radical of saturated organic acids substituted with tert-alkyl, cycloalkyl, cycloalkenyl, alkoxyl, heterocyclic and carboalkoxylradicals, or with aldehyde or hydroxy groups. These acyl-derivatives of carnitine are useful therapeutical agents in the treatment of cardiac disorders, hyperlipidaemias and hyperlipoproteinaemias.

4 Claims, No Drawings

NOVEL CLASS OF ACYL-DERIVATIVES OF CARNITINE, PROCESS FOR PREPARING SAME AND THERAPEUTIC USE THEREOF

This is a division of Ser. No. 068,748, filed on June 30, 1987, now U.S. Pat. No. 4,766,222, which is a continuation of Ser. No. 753,653, filed July 10, 1985, now abandoned, which is a continuation of Ser. No. 433,427, filed Oct. 8, 1982, now abandoned, which is a continuation of Ser. No. 237,312, filed Feb. 23, 1981, now abandoned.

The present invention relates to a novel class of acyl-derivatives of carnitine ($\beta$-hydroxy $\gamma$-butyrobetaine), a process for preparing same and the therapeutical utilization thereof.

More particularly, the present invention relates to acyl-derivatives of carnitine having general formula

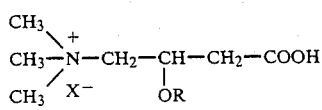

wherein:
$X^-$ is an anion, preferably a halogenide or sulfate anion, and
R is the radical of the following organic acids:

(a) unsaturated organic acids: acrylic, vinyl-acetic and allyl-acetic acid;

(b) saturated organic acids substituted with a tert-alkyl radical: tert-butyl acetic and tert-butyl propionic acid;

(c) saturated organic acids substituted with a cycloalkyl radical: cyclopentan-carboxylic, cyclopentan-acetic, cyclopentan-propionic, cyclohexyl-acetic and cyclohexyl-butyric acid;

(d) saturated organic acids substituted with a cycloalkenyl radical: 3-cyclohexene-carboxylic and 2-cyclopenten-acetic acid; (e) saturated organic acids substituted with an alkoxyl-radical: methoxy acetic and ethoxy acetic acid;

(f) saturated organic acids substituted with a carboalkoxyl radical: 3-carbomethoxy propionic and 4-carbomethoxy butyric acid;

(g) hydroxy-substituted saturated organic acids: 2-hydroxy isobutyric, 2-hydroxy isovaleric, 2-hydroxy isocaproic, 2-hydroxy-2-methyl butyric, 2-methyl-3-hydroxy-propionic, 2-hydroxy-tert-butyl-acetic, 3-hydroxy-3-methyl-glutaric (monoester), 3-hydroxy-2-methyl-glutaric (monoester) and 3-hydroxy-propionic acid;

(h) saturated organic acids substituted with an aldehyde group: 2-formyl propionic and formyl-isobutyric acid;

(i) saturated organic acids substituted with a heterocyclic radical: 1,2-dithiolane-3-pentanoic, 2-thiophene-carboxylic and 2-thiophene acetic acid.

The present invention encompasses the compounds of formula (I) both in their optically active forms (either D or L) and in their racemic form (D,L) and also encompasses their pharmacologically acceptable salts, whether they are optically active or inactive.

The compounds of formula (I) can in fact be prepared either as such or in the form of salts with mineral acids or with mono- or multi-carboxylic aliphatic and aromatic acids or with sulfonic and sulfamic acids. Generally, the compounds of formula (I) and their corresponding pharmacologically acceptable salts have shown remarkable cardiotroopic, hyperlipoproteinaemic and hyperlipidaemic activities.

The compounds of formula (I) are normally prepared in the form of chlorides.

It is in fact preferable to react $\beta$-hydroxy $\gamma$-butirobetaine chloride with the acid chloride of the appropriate acid (a) through (i) previously mentioned.

The process for preparing these novel acyl-derivatives normally takes place at a temperature comprised between 0° C. and 80° C. in an anhydrous environment and in the presence of an organic solvent selected from the group consisting of trifluoroacetic acid and the acids (a) through (i) previously listed under formula (I) corresponding to the used acid chloride. When the acid chloride is solid and is not easily soluble in said organic solvent it is possible to improve its solubility in such a way as to obtain a homogeneous phase by adding a small amount of a chlorinated solvent, such as chloroform or anhydrous methylene chloride.

Particular care will be taken in order to maintain anhydrous the environment by protecting the reaction system with suitable dehydrating means, e.g. $CaCl_2$—containing tubes.

At the end of the reaction the resulting mixture is cooled and usually treated with acetone; the solid, if any, which separates is removed, whereas the precipitate which forms by adding ethyl ether is collected.

The precipitate can be purified by crystallization with ethyl ether. Generally one or two crystallizations are sufficient to obtain a high purity product which can be easily checked by thin layer chromatography (T.L.C.) using silica plates and various eluents such as $CHCl_3$—MeOH—conc. $NH_4OH$ (50:30:8 v/v) or n-BuOH— acetic acid —$H_2O$ (60:20:20: v/v).

Generally, the reaction yields range from 60 to 85%, on condition that the yield lowering, if any, which might take place during the purification by crystallization is not taken into consideration.

The following examples, beside setting forth several chimico-physical data of some compounds of this invention, illustrate the synthesis process thereof without limiting the invention scope.

EXAMPLE 1

Preparation of tert-butyl acetyl carnitine chloride

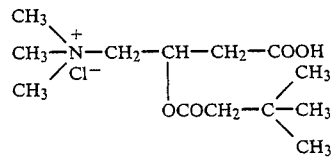

Carnitine chloride (1.97 g; 0.01 moles) was dissolved in trifluoroacetic acid (10 cc). To the solution tert-butyl acetyl chloride (1.4 cc; 0.01 moles) was slowly added under stirring. The resulting mixture was kept under stirring at room temperature for 48 hours. To te mixture $Et_2O$ was added and the thus obtained precipitate was filtered off. The raw product was crystallized from isopropanol-ethyl ether, thus obtaining a pure product. MP 164°–165° C.

Yield 80%.

NMR δ 5.6 (m, 1H, —CH—); 3.9 (d, 2H, 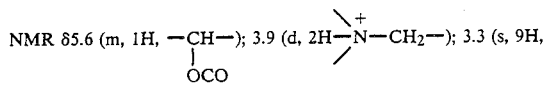); 3.3 (s, 9H,

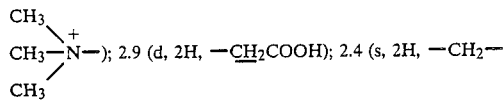 2.9 (d, 2H, —CH₂COOH); 2.4 (s, 2H, —CH₂—

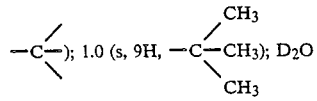 D₂O

EXAMPLE 2

(a) Preparation of cyclohexyl acetyl chloride

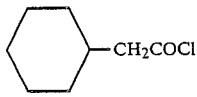

Cyclohexyl acetic acid (2.5 g; 0.02 moles) was mixed with SOCl₂ (3.7 cc; 0.05 moles) and the resulting solution was kept at 80° C. for 1.5 hours. The mixture was concentrated under vacuum and some washings were carried out with anhydrous toluene to remove SOCl₂. The mixture was then dried under vacuum and the title product was obtained as a raw material which was used as such in the next step (b).

(b) Preparation of cyclohexyl acetyl carnitine chloride

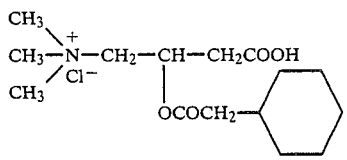

Carnitine chloride (2.97 g; 0.01 moles) was dissolved in trifluoro acetic acid (10 cc). To this solution was added cyclohexyl acetyl chloride (0.01 moles) prepared as previously disclosed and the resulting mixture was kept under stirring for 48 hours. Ethyl ether was then added and the resulting mixture was kept under stirring for 0.5 hours at 0° C. A precipitate was obtained, which was filtered off and dried under vacuum.

MP 161°-162° C., yield 70%.

NMR δ 5.6 (m, 1H, —CH—); 3.8 (m, 2H, 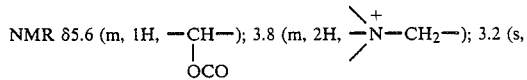); 3.2 (s,

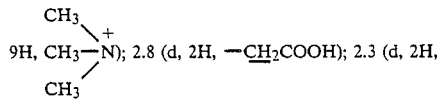 2.8 (d, 2H, —CH₂COOH); 2.3 (d, 2H,

O—COCH₂—); 2.0-0.8 (m, 11H, 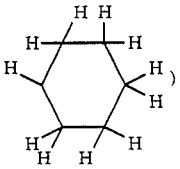)

EXAMPLE 3

Preparation of cyclopentanpropionyl carnitine chloride

Carnitine chloride (1.97 g; 0.01 moles) was dissolved in trifluoroacetic acid (10 cc). To the resulting solution 3-cyclopentanpropionyl chloride (1.60 g; 0.01 moles) was slowly added under stirring. The resulting mixture was kept under stirring at 45° C. overnight. The mixture was then cooled, acetone (40 ml) was added and the mixture was kept under stirring for 2 hours in ice. The precipitate thus formed was filtered off and to the filtrate ethyl ether was added. The white solid which precipitated was dissolved in ethanol-acetone (5:1) and once again precipitated with ether.

M.P. 170°-172° C., yield 90%.

| NMR (D₂O) | δ 5.5 | (m, 1H, CH₂—CH—CH₂) |
|---|---|---|
| | 2.8 | (d, 2H, N—CH₂) |
| | 3.2 | (s, 9H, (CH₃)₃) |
| | 2.7 | (d, 2H, CH₂—COOH) |
| | 2.4 | (t, 2H, CH₂—CH₂—⬠) |
| | 1.9-0.9 | (m, 11H, —CH₂—⬠) |

EXAMPLE 4

Preparation of vinyl acetyl carnitine chloride

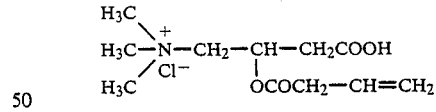

To a solution of carnitine chloride (2 g; 0.01 moles) in trifluoroacetic acid (6 ml) vinyl acetyl chloride (1.8 ml; 0.02 moles) was added under stirring at room temperature.

The reaction mixture was then brought at 50° C. and kept under reacting conditions overnight. The mixture was then cooled to room temperature and poured in ethyl ether (200 ml) and kept under stirring for 20 minutes. The ether phase was decanted and the thus obtained precipitate was taken up with acetonitrile and the resulting solution was allowed to stand for 2 hours. The unreacted carnitine, which separated in the form of a crystalline solide, was filtered off and to the filtrate ethyl ether was added. The precipitate thus formed was a white crystalline solid.

TLC (CHCl₃/MeOH/H₂O/NH₄OH, 55:35:5:5) Rf 0.55.

NMR (D₂O) δ: 2.88(2H, d-C<u>H</u>₂—COOH); 3.28(11H, m, 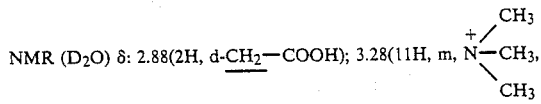

—CH₂—OCO—); 3.73-4.03(2H, m-CH₂—N<; 5.06-6.26 (4H, m,

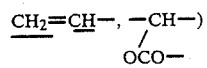

In the same NMR spectrum there were also present the following meaningful signals which were attributed to the isomer crotonoyl carnitine:

δ1.95 (3H, d.d., C<u>H</u>₃—C=); 6.64-7.38 (2H, m, —C<u>H</u>=C<u>H</u>—).

By computation of the integrals of the foregoing signals it was possible to evaluate the amount of said isomer which was present in the product in an amount of about 15-20%.

EXAMPLE 5

Preparation of ethoxyacetyl carnitine isobutylester (a) Preparation of carnitine isobutylester Carnitine chloride (10 g; 0.05 moles) was suspended in 100 ml of isobutanol. The suspension was cooled with an ice bath and gaseous HCl was bubbled therein till complete saturation was reached. The resulting mixture was kept for 2 hours under reflux conditions. The mixture was then concentrated to remove the alcohol, the concentrate was dissolved in distilled water and the solution was neutralized with IR-45 resin. The resulting product was lyophilized, thus yielding 12 g of carnitine isobutylester.

(b) Preparations of ethoxyacetic acid chloride

Thionyl chloride (1.1 cc; 0.0125 moles) was added to ethoxyacetic acid (1.3 cc; 0.012 moles). The resulting mixture was kept at room temperature for 12 hours. The reaction mixture was washed three times with a chloroform-anhydrous ethyl ether mixture and subsequently concentrated under vacuum (80 mm Hg), at 30 C. 1.15 grams of ethoxy-acetic acid chloride were obtained.

(c) Reaction between carnitine isobutylester and ethoxyacetic acid chloride.

Carnitine isobutyl ester (1.1 g; 0.043 moles) was dissolved in anhydrous acetone and to the resulting solution the ethoxyacetic acid chloride (1.15 g; 0.009 moles) was added. The reaction mixture was dried and the residue kept in an atmosphere of inert gas (argon) at room temperature for two days. The residue was then crystallized from isopropanol-ethyl ether. The title product was obtained with 65% yield.

| T.L.C. Eluent: | CHCl₃ | 40 |
| --- | --- | --- |
| | CH₃OH | 40 |
| | CH₃COONa 0.01M | 10 |
| NMR | D₂O δ 5.8 (1H, m, CH ); | |

|
OCO
4.2 (2H,s,—COC<u>H</u>₂O—); 4.0 (4H,m,
—COOCH₂—, O—C<u>H</u>₂CH₃); 3.7 (2H,d,

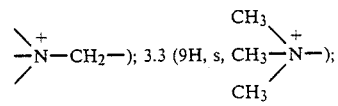

2.7 (2H, d,—C<u>H</u>₂ COO—); 1.9 (1H, m,

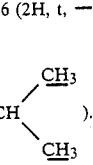

EXAMPLE 6

Preparation of 3-cyclohexenylcarboxylcarnitine chloride (a) Preparation of 3-cyclohexenecarboxyl chloride.

Cyclohexenecarboxylic acid (1.2 cc; 0.01 moles) was mixed with oxalyl chloride (0.9 cc; 0.01 moles) and the resulting mixture was kept under stirring at room temperature for 3.5 hours. The solution was then concentrated under vacuum (100 mm Hg; t=70° C.). The raw product thus obtained was used as such in the next step.

(b) Reaction of 3-cyclohexenecarboxyl chloride with carnitine chloride.

Carnitine chloride (1 g; 0.05 moles) was dissolved in trifluoroacetic acid (2 cc). To the resulting solution was slowly added under stirring, at room temperature, the chloride (0.01 moles) of the previous step. The resulting action mixture was kept under stirring for 15 hours. Ethyl ether was then added to the reaction mixture and a precipitate was obtained which was subsequently twice washed with ethyl ether to eliminate the excess of acid chloride. The precipitate was filtered and dried under vacuum.

Yield: 90%.

| T.L.C. Eluent: | CHCl₃ | 60 |
| --- | --- | --- |
| | MetOH | 40 |
| | H₂O | 15 |
| | Isopr OH | 10 |
| | CH₃COOH | 15 |
| NMR | | |

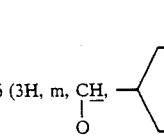

3.9 (2H, d, 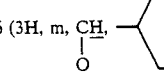

2.86(2H,d,—C<u>H</u>₂ COO—); 2.00(7H,m,<u>H</u> 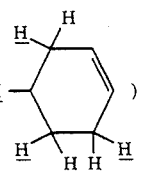 )

EXAMPLE 7

Preparation of 3-carbomethoxypropionyl carnitine chloride

To a solution of carnitine chloride (4 g; 20 m moles) in trifluoroacetic acid, 3-carbomethoxypropionyl chloride (3.0 cc; 24 m moles) was added and the resulting reaction mixture was kept under stirring at 45° C. overnight. The mixture was then cooled and ethyl ether was added. The solid which formed was crystallized from iso-propanol.

M.P. 160°–161° C.

T.L.C.: $CHCl_3MeOH/CH_3 COONa$ 40/40/20 m.u.

NMR: $D_2O=2.75$ (4H s, $CH_2-CH_2$) 2.80 (2H d, $CH_2-COOH$) 3.25 (9H s, $(CH_3)_3$) 3.70 (3H s, $COOCH_3$) 3.80 (2H d, $N-CH_2$) 5.65 (m, $-CH_2-CH-CH_2$)

EXAMPLE 8

Preparation of 4-carbomethoxy butyrul carnitine chloride

To a solution of carnitine (2.0 g; 10 m moles) in TFA (5 cc), 4-carbomethoxy butyrul chloride (1.65 cc; 12 m moles) was added and the resulting reaction mixture was kept at room temperature under stirring for 24 hours. To this mixture anhydrous ethyl ether was then added. A solid formed which was filtered off and crystallized from hot isopropanol.

M.P. 130°–132° C.

NMR $D_2O$ δ5.6(1H,m, $-\underset{\underset{OCO}{|}}{CH}-$); 3.7 (5H,m, $\overset{\diagdown}{\underset{\diagup}{N}}\!\!\!^+\!\!-CH_2,-OCH_3$);

3.2 (9H, s, $CH_3\!-\!\overset{CH_3}{\underset{CH_3}{\overset{\diagdown}{\underset{\diagup}{N}}\!\!\!^+}}\!\!-$); 2.8 (2H,d, $-\underline{CH}_2COOH$);

2.4 (4H, m, $OCO\underline{CH}_2CH_2\underline{CH}_2-COO-$);

1.9 (2H, m, $-OCO-CH_2-\underline{CH}_2-CH_2-COO$)

EXAMPLE 9

Preparation of methoxy acetyl carnitine chloride

A mixture of methoxyacetic acid (3 ml; 0.04 moles) and methoxyacetyl chloride (3 ml; 0.03 moles) was kept under stirring at 30° C. for 2 hours. To this mixture carnitine chloride (4 g; 0.02 moles) which had been previously dried was added. The resulting mixture was brought to 40° C. and kept under stirring for seven days. The mixture was then taken up with acetonitrile and the unreacted carnitine chloride was filtered off. Upon addition of tert-butyl methyl ether an oil precipitated. The oil precipitation was repeated four times with acetonitrile/tert butyl methyl ether. The oil which finally separated was lyophilized. Four grams of mthoxy acetyl carnitine chloride were thus obtained.

Yield: 75%.

NMR $D_2O$ δ 5.68 (1H, m, $-\underset{\underset{OCO}{|}}{CH}-$); 4.21 (2H, s, $-COCH_2O-$);

3.85 (2H, d, $\overset{\diagdown}{\underset{\diagup}{N}}\!\!\!^+\!\!-CH_2-$); 3.45 (3H, s, $-OCH_3$);

3.23 (9H, s, $CH_3\!-\!\overset{CH_3}{\underset{CH_3}{\overset{\diagdown}{\underset{\diagup}{N}}\!\!\!^+}}\!\!-$); 2.85 (2H, d, $-\underline{CH}_2COOH$)

EXAMPLE 10

Preparation of ethoxy acetyl carnitine chloride

A mixture of ethoxy acetic acid (5 ml; 0.07 moles) and ethoxyacetyl chloride (1.8 ml; 0.015 moles) which had been prepared as disclosed in step (b) of Example 5, was kept under stirring for 2 hours at 80° C. To this mixture carnitine chloride (2 g; 0.01 moles) which had been previously dried was added. The resulting mixture was first kept at 80° C. until complete dissolution of carnitine took place, then at 40° C. for eight days. A further amount of ethoxyacetyl chloride (0.9 ml; 0.007 moles) was added and the resulting mixture was kept at 40° C. for seven days. Upon addition to the mixture of tert-butyl methyl ether an oil precipitated. The oil precipitation was repeated four times with acetonitrile/tert butyl methyl ether until complete removal of the ethoxyacetic acid in excess. 1.5 grams of the title compound were thus obtained.

Yield: 75%.

NMR $D_2O$ δ 5.96 (1H, m, $-\underset{\underset{OCO}{|}}{CH}-$); 4.23 (2H, s, $-COCH_2-O$);

3.78–3.50 (4H, m, $\overset{\diagdown}{\underset{\diagup}{N}}\!\!\!^+\!\!-CH_2-$; $-O\underline{CH}_2CH_3$);

3.23 (9H, s, $CH_3\!-\!\overset{CH_3}{\underset{CH_3}{\overset{\diagdown}{\underset{\diagup}{N}}\!\!\!^+}}\!\!-$);

2.85 (2H, d, $-\underline{CH}_2COOH$); 1.2 (3H, t, $-OCH_2\underline{CH}_3$)

The characteristics of pharmacological activity of the compounds of general formula (I) are hereinbelow illustrated.

The acute toxicity of the compounds of general formula (I) was investigated in mice using the Weil method (Weil C. S., Biometr. J. 8, 249, 1952). The $LD_{50}$ values given in Table 1 below, show that the compounds exhibit good tolerance.

The cardiokinetic effect was investigated on rabbit hearts isolated by the Langendorff method. Rabbit hearts isolated by this method were perfused with oxygenated Ringer solution at 38.2° C. The isometric contractions, electro-cardiogram and coronary flow were recorded using a "Battaglia-Rangoni" polygraph. By removing the oxygen from the perfusion fluid, metabolic damage was induced in the cardiac muscle, up to an 80% reduction in the cardiac contractile force.

Under these conditions of prolonged anoxia the aerobic glycolysis of the myocardium is sowed down with attendant formation of acid catabolites due to both the accumulation of pyruvic acid and its conversion to lactic acid which cannot be utilized because of the depression of pyridine enzymes, such as LDH (lactodehydrogenase). This has repercussions on the anaerobic glycolysis affecting an ever increasing number of enzymes, accompanied by a progressive and increasingly critical exhaustion of the myocardium. Thus a whole series of cardiac muscle fatigue levels occurs which can be observed by the behaviour of the examined parameters, namely the contractile force, coronary flow, heart rate and cardiac rhythm. As soon as the contractile force was reduced by 80%, the perfusion fluid was once again oxygenated either without adding other compounds (controls) or with the addition of the compounds under examination.

Table II below gives the percentage values of the contractile force of the heart, showing a positive inotropic effect, calculated after 10 minutes from the interruption of the anoxic period (myocardial restoration).

The antiarrhythmic effect of the compounds was also investigated in mice according to the P. W. Nwangwu, T. Holcslow procedure (P. W. Nwangwu, T. L. Holcslow; Arch. Int. Pharmacodyn. 229, 219 (1977)). Using aconitine (5 γ/ml) as arrhythmogenic agent, the changes in the cardiac rhythm of the animals were recorded and the onset time of initial arrhythmia and/or of ventricular tachycardia were used as end point. The results are summarized in Table III.

The effect of the compounds on the modification of the lipoprotein pattern as well as on the levels of plasma chlolesterol and triglycerides, altered by oral administration of olive oil, was investigated in normally fed rats, treated orally with olive oil, 15 ml kg$^{-1}$, 1 hour before the oral administration of the compound, and with the compounds at various concentrations.

The most important effect, after two hours from olive administration, which entailed an increase in triglycerides and cholesterol with reduction of α lipoproteins and increase of the β and pre-β fractions, was well antagonized by some compounds which, as shown in Table IV, proved to be able to restore to normal the foregoing parameters widely reaching the limits of statistical significativity.

TABLE I

LD50, mg kg$^{-1}$ i.p. in mice of some acyl derivatives of general formula (I). Weil method (N = 5,K = 4)

| Compounds | LD50 | and fiducial limits |
|---|---|---|
| acrilyl-CAR | 1380 | (950–1800) |
| vinyl-CAR | 1200 | (800–1600) |
| tert-butyl ACAR | 1115 | (789–1440) |
| cyclohexyl ACAR | 850 | (572–1128) |
| cyclohexyl-butyryl CAR | 925 | (675–1175) |
| 2-cyclopenten ACAR | 1200 | (850–1550) |
| ethoxyacetyl CAR | 760 | (545–975) |
| 3-carbomethoxypropionyl CAR | 985 | (709–1260) |
| 2-hydroxy isobutyryl CAR | 1470 | (1170–1770) |

TABLE I-continued

LD50, mg kg$^{-1}$ i.p. in mice of some acyl derivatives of general formula (I). Weil method (N = 5,K = 4)

| Compounds | LD50 | and fiducial limits |
|---|---|---|
| 2-hydroxy isovaleryl CAR | 1585 | (1227–1943) |
| formyl propionyl CAR | 1010 | (850–1170) |
| ethoxy ACAR | 2120 | (1820–2420) |
| methoxy ACAR | 1980 | (1630–2330) |
| monomethylglutaryl CAR | 1870 | (1620–2120) |

TABLE II

Effect of some acyl derivatives of carnitine, having general formula (I) on the contractile force of rabbit's heart "in vitro".

| Compounds | concentration | contractile force mean ± ESM | P |
|---|---|---|---|
| Krebs. (control) | — | 26.93 ± 5.31 | |
| acrilyl CAR | 10$^{-6}$ M | 55.31 ± 4.36 | ≦0.01 |
| vinyl CAR | 10$^{-6}$ M | 48.25 ± 5.12 | ≦0.01 |
| tert-butyl ACAR | 10$^{-6}$ M | 59.33 ± 5.26 | ≦0.001 |
| cyclohexyl ACAR | 10$^{-6}$ M | 43.18 ± 4.81 | ≦0.05 |
| cyclohexyl butyryl CAR | 10$^{-6}$ M | 42.15 ± 4.17 | ≦0.05 |
| 2-cyclopentenyl ACAR | 10$^{-6}$ M | 59.83 ± 3.26 | ≦0.01 |
| ethoxyacetyl CAR | 10$^{-6}$ M | 62.25 ± 3.24 | ≦0.01 |
| 3-carbomethoxypropionyl CAR | 10$^{-6}$ M | 70.35 ± 5.23 | ≦0.001 |
| 2-hydroxy isobutyryl CAR | 10$^{-6}$ M | 73.88 ± 4.12 | ≦0.001 |
| 2-hydroxy isovaleryl CAR | 10$^{-6}$ M | 82.53 ± 4.09 | ≦0.001 |
| formyl propionyl CAR | 10$^{-6}$ M | 74.26 ± 4.15 | ≦0.001 |
| ethoxy ACAR | 10$^{-6}$ M | 78.15 ± 3.12 | ≦0.001 |
| methoxy ACAR | 10$^{-6}$ M | 81.25 ± 4.08 | ≦0.001 |
| monomethylglutaryl CAR | 10$^{-6}$ M | 58.12 ± 4.25 | ≦0.01 |

TABLE III

Effect of some acyl derivatives of carnitine having general formula (I) on the arrythmia induced by Aconitine in mice. % increase of the latency time to onset of initial cardiac arrhythmia and tachycardia with respect to the control group.

| Compounds | concentrations mg kg$^{-1}$ i.v. | latency time for arrythmias | tachycardia |
|---|---|---|---|
| acryl CAR | 50 | 45 | 39 |
| vinyl CAR | 38 | 53 | 41 |
| tert-butyl ACAR | 25 | 59 | 36 |
| cyclohexyl ACAR | 35 | 63 | 44 |
| cyclohexyl butyryl ACAR | 50 | 48 | 32 |
| cyclopentenyl ACAR | 100 | 40 | 20 |
| ethoxyacetyl CAR | 100 | 40 | 20 |
| 3-carbomethoxy propionyl CAR | 25 | 65 | 39 |
| 2-hydroxy isobutyryl CAR | 25 | 55 | 48 |
| 2-hydroxy isovaleryl CAR | 40 | 60 | 30 |
| formyl propionyl CAR | 60 | 55 | 34 |
| ethoxy ACAR | 20 | 60 | 55 |
| methoxy ACAR | 25 | 65 | 50 |
| monomethylglutaryl CAR | 30 | 52 | 40 |
| Quinidine | 8.9 | 50 | 41.7 |

TABLE IV

Effect of some acyl-carnitine derivatives of general formula (I) on plasma cholesterol (Chol.) triglycerides (TG) and α-, β- and pre-β -lipoproteins in rats treated with olive oil, 15 ml kg$^{-1}$ orally, 1 hour before compound administration

| Compounds | mg kg$^{-1}$ | oil ml kg$^{-1}$ | TG mg/100 ml | Chol. mg/100 ml |
|---|---|---|---|---|
| Blank | — | — | 75.12 ± 6.15 | 65.15 ± 6.18 |
| Control | — | 15 | 215.36 ± 20.18 | 96.18 ± 4.16 |
| vinyl CAR | 300 | 15 | 112.15 ± 15.16n.s. | 78.15 ± 6.16n.s. |
| tert-butyl CAR | 350 | 15 | 99.36 ± 10.12 | 70.12 ± 3.24Δ |
| cyclohexyl CAR | 400 | 15 | 100.12 ± 15.16Δ | 85.15 ±4.26n.s. |
| 3-carbomethoxypropionyl CAR | 350 | 15 | 88.15 ± 15.36 | 69.25 ± 3.26 |
| 2-hydroxy isobutyryl CAR | 450 | 15 | 100.29 ± 12.48 | 75.03 ± 4.12Δ |
| ethoxy ACAR | 250 | 15 | 78.25 ± 10.12 | 70.26 ± 6.48 |
| methoxy ACAR | 300 | 15 | 85.14 ± 13.26 | 72.12 ± 6.87 |

TABLE IV-continued

Effect of some acyl-carnitine derivatives of general formula (I) on plasma cholesterol (Chol.) triglycerides (TG) and α-, β- and pre-β -lipoproteins in rats treated with olive oil, 15 ml kg$^{-1}$ orally, 1 hour before compound administration

| | | | | |
|---|---|---|---|---|
| monomethylglutaryl CAR | 400 | 15 | 120.36 ± 14.15 | 81.27 ± 5.92 n.s. |

| Compounds | mg kg$^{-1}$ | oil ml kg$^{-1}$ | % Lipoproteins | | |
|---|---|---|---|---|---|
| | | | α | β | pre-β |
| Blank | — | — | 36.15 ± 2.12 | 10.15 ± 1.23▲ | 49.22 ± 2.17▲ |
| Control | — | 15 | 23.28 ± 2.19 | 16.12 ± 1.48 | 56.45 ± 2.36 |
| vinyl CAR | 300 | 15 | 29.46 ± 3.15n.s. | 14.13 ± 1.63n.s. | 48.89 ± 2.96n.s. |
| tert-butyl CAR | 350 | 15 | 31.12 ± 2.17□ | 13.27 ± 1.12□ | 51.36 ± 2.11□ |
| cyclohexyl CAR | 400 | 15 | 36.48 ± 2.36 | 12.15 ± 1.09 | 49.12 ± 2.17▲ |
| 3-carbomethoxypropionyl CAR | 350 | 15 | 34.17 ± 3.23 | 11.18 ± 1.15 | 50.03 ± 2.09▲ |
| 2-hydroxy isobutyryl CAR | 450 | 15 | 27.19 ± 3.48n.s. | 10.36 ± 1.12 | 48.36 ± 1.15 |
| ethoxy ACAR | 250 | 15 | 37.15 ± 2.17 | 10.28 ± 1.52 | 42.15 ± 2.27 |
| methoxy ACAR | 300 | 15 | 36.39 ± 3.12 | 12.32 ± 1.65 | 45.83 ± 3.46 |
| monomethylglutaryl CAR | 400 | 15 | 35.28 ± 3.94n.s. | 14.25 ± 1.83n.s. | 51.12 ± 4.15n.s. |

Student "t" test for the difference with respect to the control
□, ▲ e indicate respectively P ≦ 0.05, 0.01 and 0.001. N = 6

PHARMACEUTICAL PREPARATIONS

1. Solutions and sterile aqueous solutions containing acyl-carnitines of formula (I) in concentrations from 25 mg to 500 mg per ml.

(a) The excipient for injectable ampoules/vials is prepared in accordance with the following non-limitative composition:

| | |
|---|---|
| sodium carboxymethyl cellulose (at low viscosity) | 10 mg/ml |
| polysorbate 80 | 4 mg/ml |
| propylparaben | 0.4 mg/ml |
| water for injections sufficient for 1 ml, 2 ml, 5 ml and 10 ml ampoules/vials | |

(b) The excipient for phleboclysis bottles containing 50 ml, 100 ml, 250 ml, 500 ml and 1000 ml is prepared in accordance with the following non-limiting composition:

| | |
|---|---|
| NaCl | 8.6 g/l |
| KCl | 0.3 g/l |
| CaCl$_2$ | 0.33 g/l |
| water for injections sufficient for 1 liter. | |

(c) The excipient for bottles for oral use containing from 5 ml to 100 ml is prepared in accordance with the following non-limiting composition:

| | |
|---|---|
| mannitol | 11 mg/ml |
| sorbitol | 600 mg/ml |
| sodium benzoate | 3 mg/ml |
| orange extract | 200 mg/ml |
| vitamin B$_{12}$ | 3 mcg/ml |
| sufficient purified water | |

2. Tablets containing from 20 mg to 500 mg of acyl-carnitine of formula (I). The excipient is prepared in accordance with the following non-limiting composition:

| | |
|---|---|
| starch | 45% |
| avicel | 45% |
| talc | 10% |

3. Capsules containing from 20 mg to 500 mg of acyl-carnitine of formula (I) without excipients.

4. Aerosol and spray preparations from 500 mg to 10 g of an acyl-carnitine of formula (I). The excipient is prepared in accordance with the following non-limiting composition:

| | |
|---|---|
| ethanol | 30% |
| purified water | 30% |
| sufficient freon 12/114 | (50 parts/50 parts). |

What is claimed is:

1. An acyl-derivative of carntine or pharmaceutically acceptable salt thereof, having the general formula

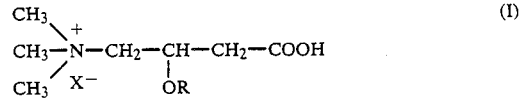

(I)

wherein x is an anion, and R is the radical of one of the following organic acids: dithiolane 3-pentanoic, or 2-thiophenecarboxylic or 2-thiopheneacetic acid.

2. The acyl derivatives of the carnitine of claim 1 in their optically active forms.

3. The acyl derivatives of the carnitines of claim 1 in the in their racemic form.

4. A pharmaceutically acceptable composition for treating cardiac disorders, hyperlipoproteinaemias and hyperlipidaemias, comprising a pharmaceutically acceptable amount of An acyl-derivative of carntine or pharmaceutically acceptable salt thereof, having the general formula

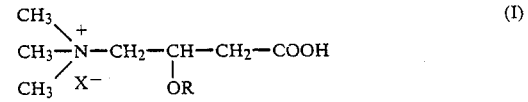

(I)

wherein x is an anion, and R is the radical of one of the following organic acids: dithiolane 3-pentanoic, or 2-thiophenecarboxylic or 2-thiopheneacetic acid.

* * * * *